(12) United States Patent
Yokota

(10) Patent No.: US 10,342,459 B2
(45) Date of Patent: Jul. 9, 2019

(54) ENDOSCOPE APPARATUS AND MEASURING METHOD

(71) Applicant: OLYMPUS CORPORATION, Hachioji-shi, Tokyo (JP)

(72) Inventor: Masayoshi Yokota, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 165 days.

(21) Appl. No.: 15/423,043

(22) Filed: Feb. 2, 2017

(65) Prior Publication Data

US 2017/0143237 A1    May 25, 2017

Related U.S. Application Data

(60) Division of application No. 14/061,530, filed on Oct. 23, 2013, now abandoned, which is a continuation of
(Continued)

(30) Foreign Application Priority Data

Apr. 27, 2011 (JP) ................................ 2011-099889
Apr. 27, 2011 (JP) ................................ 2011-099890

(51) Int. Cl.
*A61B 1/00* (2006.01)
*A61B 5/107* (2006.01)
(Continued)

(52) U.S. Cl.
CPC ........ *A61B 5/1077* (2013.01); *A61B 1/00009* (2013.01); *A61B 1/00045* (2013.01);
(Continued)

(58) Field of Classification Search
CPC .......... H04N 5/2256; H04N 2005/2255; G06T 7/521; G02B 23/2469; A61B 1/00096;
(Continued)

(56) References Cited

U.S. PATENT DOCUMENTS 5,150,254 A    9/1992 Saitou
5,434,669 A    7/1995 Tabata et al.
(Continued)

FOREIGN PATENT DOCUMENTS

DE    10104483 A1    10/2002
EP    2106748 A1    10/2009
(Continued)

OTHER PUBLICATIONS

Non-Final Office Action dated Feb. 25, 2016 issued in parent U.S. Appl. No. 14/061,530.
(Continued)

*Primary Examiner* — Timothy J Neal
(74) *Attorney, Agent, or Firm* — Holtz, Holtz & Volek PC

(57) ABSTRACT

An endoscope apparatus measuring a subject using a pattern projection image of the subject on which a light and dark pattern of light is projected, includes an insertion tube; an image sensor; an objective optical system forming the subject image on the image sensor; an illumination light source illuminating the subject; a pattern projector projecting the light and dark pattern onto the subject; and a projection window disposed at a distal end portion of the insertion tube. When the projection window is viewed from the front and the distal end portion of the insertion tube is divided into two sides by an imaginary first plane which includes a central axis of the insertion tube, a center of the projection window is at one of the two sides of the distal end portion of the insertion tube. An observation window is disposed at the distal end portion of the insertion tube. When the projection window is viewed from the front, a center of the observation window is disposed at the other of the two sides of the distal end portion of the insertion tube.

6 Claims, 9 Drawing Sheets

Related U.S. Application Data application No. PCT/JP2012/060832, filed on Apr. 23, 2012.

(51) Int. Cl.

| | | |
|---|---|---|
| *G02B 23/24* | (2006.01) | |
| *A61B 1/05* | (2006.01) | |
| *A61B 1/06* | (2006.01) | |
| *A61B 5/00* | (2006.01) | |
| *G06T 7/521* | (2017.01) | |
| *H04N 5/225* | (2006.01) | |

(52) U.S. Cl.
 CPC ...... *A61B 1/00096* (2013.01); *A61B 1/00179* (2013.01); *A61B 1/00193* (2013.01); *A61B 1/05* (2013.01); *A61B 1/0676* (2013.01); *A61B 5/0084* (2013.01); *A61B 5/1076* (2013.01); *G02B 23/2423* (2013.01); *G02B 23/2469* (2013.01); *G06T 7/521* (2017.01); *H04N 5/2256* (2013.01); *H04N 2005/2255* (2013.01)

(58) Field of Classification Search
 CPC ....... A61B 1/00179; A61B 1/05; A61B 1/676; A61B 1/0009; A61B 1/00045; A61B 5/1077; A61B 5/0084
 See application file for complete search history.

(56) References Cited

U.S. PATENT DOCUMENTS

| | | | |
|---|---|---|---|
| 5,436,655 A * | 7/1995 | Hiyama | A61B 1/00193 348/139 |
| 5,784,098 A | 7/1998 | Shoji et al. | |
| 6,419,626 B1 | 7/2002 | Yoon | |
| 6,464,633 B1 | 10/2002 | Hosoda et al. | |
| 2005/0061062 A1 | 3/2005 | Kaneko et al. | |
| 2009/0225321 A1 | 9/2009 | Bendall et al. | |
| 2009/0225333 A1 | 9/2009 | Bendall et al. | |
| 2009/0244260 A1 | 10/2009 | Takahashi et al. | |
| 2010/0063355 A1 | 3/2010 | Matsuura | |
| 2010/0149315 A1 | 6/2010 | Qu et al. | |
| 2011/0267444 A1 | 11/2011 | Yamaguchi | |
| 2014/0052005 A1 | 2/2014 | Yokota | |
| 2014/0071239 A1 | 3/2014 | Yokota | |
| 2014/0071257 A1 | 3/2014 | Yokota | |

FOREIGN PATENT DOCUMENTS

| | | |
|---|---|---|
| EP | 2272417 A1 | 1/2011 |
| JP | 63200115 A | 8/1988 |
| JP | 01209415 A | 8/1989 |
| JP | 02085706 A | 3/1990 |
| JP | 02287311 A | 11/1990 |
| JP | 03128043 A | 5/1991 |
| JP | 05045132 A | 2/1993 |
| JP | 05211988 A | 8/1993 |
| JP | 09061132 A | 3/1997 |
| JP | 10239031 A | 9/1998 |
| JP | 10239034 A | 9/1998 |
| JP | 2005091265 A | 4/2005 |
| JP | 2007139822 A | 6/2007 |
| JP | 2007144024 A | 6/2007 |
| JP | 2008229025 A | 10/2008 |
| JP | 2009019941 A | 1/2009 |
| JP | 2009061014 A | 3/2009 |
| JP | 2009240621 A | 10/2009 |
| JP | 2009258273 A | 11/2009 |
| WO | 03105289 A2 | 12/2003 |
| WO | 2007102195 A1 | 9/2007 |

OTHER PUBLICATIONS

Requirement for Restriction/Election dated Aug. 26, 2015 issued in parent U.S. Appl. No. 14/061,530.
European Office Action dated Apr. 4, 2016, issued in counterpart European Application No. 12777405.7.
Extended European Search Report dated Apr. 15, 2014 in counterpart European Application No. 12789379.0.
Extended European Search Report dated May 20, 2014 in counterpart European Application No. 12777405.7.
Final Office Action dated Sep. 6, 2016, in U.S. Appl. No. 14/061,530.
International Search Report (ISR) dated Jul. 10, 2012, issued in counterpart International Application No. PCT/JP2012/063258.
International Search Report (ISR) dated Jul. 10, 2012, issued in counterpart International Application No. PCT/JP2012/063266.
International Search Report (ISR) dated Jul. 24, 2012, issued in counterpart International Application No. PCT/JP2012/060832.
Japanese Office Action (and English translation thereof) dated Mar. 3, 2015, issued in counterpart Japanese Application No. 2011-116141.
Japanese Office Action (and English translation thereof) dated May 7, 2015, issued in counterpart Japanese Application No. 2011-099889.
Office Action dated May 5, 2016, issued in U.S. Appl. No. 14/085,726.
U.S. Appl. No. 14/061,530; First Named Inventor: Masayoshi Yokota; Title: "Endoscope Apparatus and Measuring Method"; filed Oct. 23, 2013.
U.S. Appl. No. 14/078,223; First Named Inventor: Masayoshi Yokota; Title: "Endoscope"; filed Nov. 12, 2013.
U.S. Appl. No. 14/085,726; First Named Inventor: Masayoshi Yokota; Title: "Endoscope Device, and Measurement Method"; filed Nov. 20, 2013.
Non-Final Office Action dated Oct. 5, 2018 issued in U.S. Appl. No. 15/450,741.

* cited by examiner

ENDOSCOPE APPARATUS AND MEASURING METHOD

CROSS-REFERENCE TO RELATED APPLICATIONS

This is a Divisional of U.S. application Ser. No. 14/061,530, filed Oct. 23, 2013, which is a Continuation of PCT/JP2012/060832, filed Apr. 23, 2012, which is based upon and claims the benefit of priority from prior Japanese Patent Application Nos. 2011-099889 and 2011-099890, filed Apr. 27, 2011, the entire contents of all of which are incorporated herein by reference.

BACKGROUND OF THE INVENTION

Field of the Invention

The present invention relates to an endoscope apparatus and a measuring method, and more particularly, to an endoscope apparatus that projects patterns, such as a fringe, onto a subject, to measure the three-dimensional shape of the surface of the subject, and a method of projecting patterns, such as a fringe, onto a subject, to measure the three-dimensional shape of the surface of the subject.

This application is a continuation application based on a PCT Patent Application No. PCT/JP2012/060832, filed on Apr. 23, 2012, whose priority is claimed on Japanese Patent Application No. 2011-099889, filed on Apr. 27, 2011 and Japanese Patent Application No. 2011-099890, filed on Apr. 27, 2011. The contents of both the PCT Application and the Japanese Applications are incorporated herein by reference.

Description of Related Art

In the related art, in order to inspect a subject, there are endoscopes (endoscope apparatuses) including an elongated insertion section and having observation means, such as an optical system and an imaging element, at the tip of an insertion section. Among such endoscopes, there is known an endoscope that acquires a plurality of fringe images obtained by projecting a fringe onto a subject while shifting the phase of the fringe, and that calculates the three-dimensional shape of the subject by a well-known phase shift method using the plurality of fringe images. For example, United States Patent Application, Publication No. 2009-0225321 discloses an endoscope apparatus in which two projection windows used to project a fringe are provided in a tip surface of the insertion section.

SUMMARY OF THE INVENTION

According to a first aspect of the present invention, an endoscope apparatus is provided to measure a subject using a pattern projection image of the subject on which a light and dark pattern of light is projected. The endoscope apparatus according to the first aspect of the invention includes an insertion section, an imaging section, an illumination section, and a pattern projection section. The imaging section is provided at a tip portion of the insertion section to acquire the image of the subject. The illumination section emits illumination light that illuminates an observation visual field of the imaging section. The pattern projection section projects the light and dark pattern onto the subject. A tip surface of the insertion section is provided with an objective optical system that forms the image of the subject on the imaging section, one or more illumination windows through which the illumination light is emitted, and a projection window through which the light and dark pattern is projected onto the subject from the pattern projection section. The pattern projection section includes a pattern generator which generates the light and dark pattern. The light and dark pattern is a pattern with an intensive distribution in which a light portion and a dark portion are alternately arranged.

According to a second aspect of the present invention, the objective optical system according to the first aspect of the present invention may be arranged so that an optical axis on an emission side that is directed to the imaging section from the objective optical system among optical axes of the objective optical system is parallel to and eccentric from a central axis of the insertion section.

According to a third aspect of the present invention, the objective optical system according to the second aspect of the present invention may be a direct-view-type objective optical system in which both an optical axis on an incidence side and the optical axis on the emission side are parallel to the central axis. Moreover, the objective optical system may be provided at the tip surface of the tip portion of the insertion section and is arranged at a position eccentric from the central axis.

According to a fourth aspect of the present invention, the projection window according to the third aspect of the present invention may be provided at the tip surface of the tip portion of the insertion section and is arranged at a position eccentric from the central axis of the insertion section.

According to a fifth aspect of the present invention, the objective optical system according to the second aspect of the present invention may be a side-view-type objective optical system that is exposed to an outer peripheral surface of the tip portion of the insertion section and has an optical axis on an incidence side arranged at a twisted position with respect to the central axis of the insertion section.

According to a sixth aspect of the present invention, the projection window according to the fifth aspect of the present invention may be exposed to an outer peripheral surface of the tip portion of the insertion section, and a centerline extending in the thickness direction of the projection window through the center of the projection window when the projection window is viewed from the thickness direction of the projection window may be arranged at a twisted position with respect to the central axis of the insertion section.

According to a seventh aspect of the present invention, the objective optical system according to the second aspect of the present invention may be a side-view-type objective optical system that is exposed to an outer peripheral surface of the tip portion of the insertion section and has an optical axis on an incidence side arranged to intersect the central axis of the insertion section. Moreover, the projection window may be arranged in the outer peripheral surface of the tip portion of the insertion section so that the center of the projection window when the projection window is viewed from the thickness direction of the projection window is present in a plane defined by the central axis of the insertion section and the optical axis on the incidence side.

According to an eighth aspect of the present invention, the pattern projection section according to the first aspect of the present invention may have one or more linear parallel patterns.

According to a ninth aspect of the present invention, the pattern projection section according to the first aspect of the present invention may include a projecting light source, and a pattern generator that changes the intensity distribution of the light emitted from the projecting light source and generates the light and dark pattern.

According to a tenth aspect of the present invention, the endoscope apparatus according to the ninth aspect of the present invention may further include an optical fiber that guides the light emitted from the projecting light source to the pattern generator. Moreover, the projecting light source may be provided on a base end side of the insertion section, and the pattern generator may be provided at the tip portion of the insertion section.

According to an eleventh aspect of the present invention, the projecting light source and the pattern generator according to the ninth aspect of the present invention may be provided at the tip portion of the insertion section.

According to a twelfth aspect of the present invention, the endoscope apparatus according to the ninth aspect of the present invention may further include an optical fiber that guides the light and dark pattern emitted from the projecting light source and generated by the pattern generator to a tip side of the insertion section. Additionally, the projecting light source and the pattern generator may be provided on a base end side of the insertion section.

According to a thirteenth aspect of the present invention, the endoscope apparatus according to the ninth aspect of the present invention may further include an optical adapter capable of being detachably mounted on the tip portion of the insertion section, and the pattern generator may be provided in the optical adapter.

According to a fourteenth aspect of the present invention, the projecting light source according to the thirteenth aspect of the present invention may be provided in the optical adapter.

According to a fifteenth aspect of the present invention, the endoscope apparatus according to any of the first embodiment to the fourteenth aspect of the present invention may further include switching means that switches between the light for projecting the light-and-dark-pattern and the illumination light.

According to a sixteenth aspect of the present invention, a measuring method is provided to perform the three-dimensional shape measurement of a subject using an endoscope (an endoscope apparatus). The measuring method according to the sixteenth aspect of the present invention includes projecting a predetermined light and dark pattern onto the subject from one place of the endoscope; imaging a portion of the subject onto which the light and dark pattern is projected, and acquiring at least one sheet of a pattern projection image; and using the pattern projection image to perform a three-dimensional shape measurement of the portion onto which the light and dark pattern is projected.

According to a seventeenth aspect of the present invention, a measuring method is provided to perform the three-dimensional shape measurement of a subject using an endoscope apparatus. The measuring method according to the seventeenth aspect of the present invention includes projecting a predetermined fringe pattern onto the subject from one place of the endoscope apparatus; imaging a portion of the subject onto which the fringe pattern is projected, and acquiring one sheet of a fringe image; and measuring the three-dimensional shape of the portion onto which the fringe pattern is projected, from the one sheet of fringe image, using a spatial phase shift method or a Fourier transform method.

According to an eighteenth aspect of the present invention, the measuring method according to the seventeenth aspect of the present invention may further include acquiring at least one sheet of a bright field image of the portion onto which the fringe pattern is projected, at least either before or after the one sheet of fringe image is acquired; selecting at least two sheets of images from the one sheet of fringe image and the bright field image; and detecting that a position of the endoscope apparatus has deviated when there is a positional deviation equal to or more than a predetermined amount in the two sheets of images.

According to a nineteenth aspect of the present invention, the measuring method according to the eighteenth aspect of the present invention may further include acquiring at least one sheet of the bright field images before and after the one sheet of fringe image is acquired.

According to a twentieth aspect of the present invention, in the measuring method according to the nineteenth aspect of the present invention, at least two sheets of images selected to detect that the position of the endoscope apparatus has deviated are selected from the bright field images.

Effects of the Invention

According to the endoscope apparatuses according to all of the aspects of the present invention, the diameter of the insertion section can be reduced.

According to the measuring methods according to the aspects of the present invention, the three-dimensional shape measurement is capable of being performed with high precision even in the endoscope apparatus in which the diameter of the insertion section is reduced.

According to the measuring methods of the three-dimensional shape measurement according to the aspects of the present invention, the three-dimensional shape measurement can be performed by analyzing one sheet of a fringe image captured using the endoscope apparatus. Thus, the three-dimensional shape measurement can be performed in a short period of time using the endoscope apparatus.

DETAILED DESCRIPTION OF THE INVENTION

First Embodiment

An endoscope apparatus 1 and a measuring method of the first embodiment of the invention will be described below.

Figure 1:
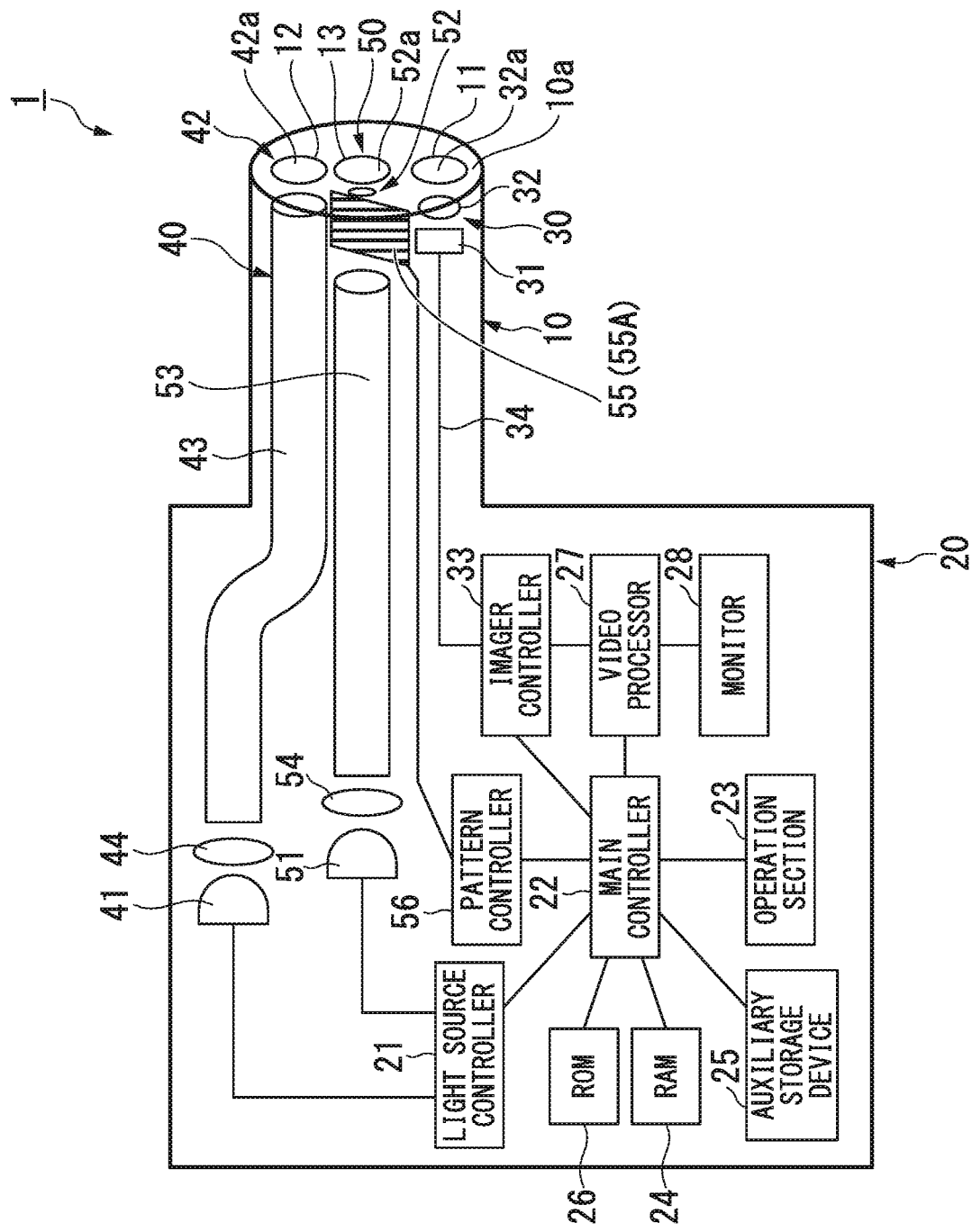
FIG. 1 is a block diagram showing the configuration of an endoscope apparatus according to a first embodiment and a second embodiment of the present invention.
Figure 2:
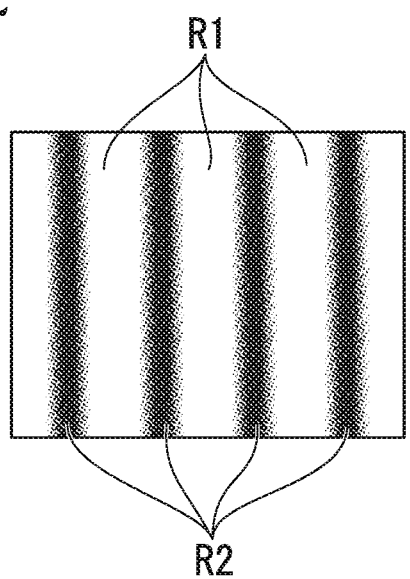
FIG. 2 is a schematic view showing a light and dark pattern projected by the endoscope apparatus according to the first and the second embodiments of the present invention.

First, the configuration of the endoscope apparatus 1 of the present embodiment will be described. FIG. 1 is a block diagram showing the configuration of the endoscope apparatus 1 of the present embodiment. FIG. 2 is a schematic view showing a light and dark pattern projected by the endoscope apparatus 1.

The endoscope apparatus 1 is used for internal observation of a subject, observation of a subject at a position where it is difficult for an ordinary observation instrument to make an access, or the like. The endoscope apparatus 1 includes an elongated insertion section 10 and a body section 20 to which a base end of the insertion section 10 is connected.

As shown in FIG. 1, the insertion section 10 is formed in a tubular shape, and inserted into the inside of a subject or an access path to a subject. The insertion section 10 is provided with an imaging section 30 that acquires the image of a subject, an illumination section 40 that illuminates an observation visual field in front of the insertion section 10, and a pattern projection section 50 that projects a light and dark pattern onto a subject. In the present embodiment, the pattern projection section 50 projects a fringe pattern onto a subject as the light and dark pattern.

Additionally, a tip surface 10a of the insertion section 10 is provided with an opening 11 for making daylight incident on an objective optical system 32 of the imaging section 30 there through, an illumination window 12 which allows the illumination light from the illumination section 40 to be irradiated toward the front of the insertion section therethrough, and a projection window 13 which allows the fringe from the pattern projection section 50 to be irradiated toward the front of the insertion section therethrough.

The imaging section 30 includes an imager 31 arranged in the vicinity of the tip of the insertion section 10, the objective optical system 32 arranged in front of the imager 31, and an imager controller 33 connected to the imager 31.

As the imager 31, various well-known configurations including various image sensors, such as a CCD and a CMOS, can be appropriately selected and used.

The objective optical system 32 is arranged within the opening 11 of the insertion section 10. The objective optical system has a predetermined angle of view, causes the reflected light within an observation visual field defined by the angle of view to be incident on the imager 31, and causes the image of a subject to be formed on the imager. Additionally, the objective optical system 32 has a light-transmissive cover member 32a that seals the opening 11.

The imager controller 33 is provided within the body section 20, and is connected to the imager 31 by a wiring line 34 extending within the insertion section 10. The imager controller 33 performs various kinds of control, such as setting by which driving and the video signals of the imager 31 are acquired.

The illumination section 40 includes a first light source 41, an illumination optical system 42, a first fiber bundle 43 that guides the light from the first light source 41 to the illumination optical system 42, a first incidence optical system 44 arranged between the first light source 41 and the first fiber bundle 43.

The first light source 41 is a general white light source, and is arranged inside the body section 20. As the first light source 41, light-emitting elements, such as an LED and a laser, a halogen lamp, or the like can be adopted.

The illumination optical system 42 is attached to the tip of the insertion section 10 or the vicinity of the tip. The illumination optical system 42 has a light-transmissive cover member 42a provided within the illumination window 12 of the insertion section 10, and a lens group that is not shown. The illumination optical system 42 broadens the light irradiated from the first light source 41 to a visual field range suitable for the angle of view of the objective optical system 32 and causes the light to be emitted from the illumination window 12, and illuminates the observation visual field thoroughly.

The first fiber bundle 43 extends from the vicinity of the illumination optical system 42 through the insertion section 10 to the first light source 41 within the body section 20. The type of the first fiber bundle 43 is not particularly limited, and a general light guide can be used.

The first incidence optical system 44 converges the light emitted from the first light source 41 up to a diameter nearly equal to the diameter of the first fiber bundle 43, and efficiently introduces the light into the first fiber bundle 43.

The pattern projection section 50 includes a second light source 51 (projecting light source), a projection optical system 52, a second fiber bundle 53 that guides the light of the second light source 51 to the projection optical system 52, a second incidence optical system 54 arranged between the second light source 51 and the second fiber bundle 53, and a pattern generator 55 arranged on an optical path for the light emitted from the second light source 51.

The second light source 51 is a white light source similar to the first light source 41, and is arranged inside the body section 20. In addition, the second light source 51 may be a light source that emits light with a wavelength different from that of the first light source 41.

The projection optical system 52 is attached to the tip of the insertion section 10 or the vicinity of the tip. The projection optical system 52 has a light-transmissive cover member 52*a* provided within the projection window 13 of the insertion section 10. The cover member 52*a* provided in the projection window 13 may be lens-shaped. The projection optical system 52 expands the light irradiated from the second light source 51 to a visual field range suitable for the angle of view of the objective optical system 32, and projects the light into an observation visual field from one projection window 13.

The second fiber bundle 53 extends from the vicinity of the projection optical system 52 through the insertion section 10 to the vicinity of the second light source 51 within the body section 20. As the second fiber bundle 53, a general light guide can be used, similar to the first fiber bundle 43.

The second incidence optical system 54 converges the light emitted from the second light source 51 up to a diameter nearly equal to the diameter of the second fiber bundle 53, and efficiently introduces the light into the second fiber bundle 53.

As the pattern generator 55, a well-known configuration capable of forming a plurality of phase-shifted fringe patterns can be used. For example, a configuration in which a slit plate having a plurality of slits is moved by an actuator, or a configuration in which a transparent plate made of glass or resin, on which a plurality of mutually phase-shifted fringe patterns are drawn, is moved by the actuator is used.

In addition, a liquid crystal shutter module capable of switching between transmission and non-transmission of light for every element, a MEMS (microelectronics system) mirror module including a fine reflective mirror for every element, or the like may be used as the pattern generator 55. In this case, since every element is controlled individually, a plurality of phase-shifted fringe patterns can be formed without moving the entire pattern generator 55. Therefore, there is an advantage that the configuration of the pattern projection section 50 can be simplified. The switching among the fringe patterns is performed by a pattern controller 56 connected to the pattern generator 55.

Figure 9:
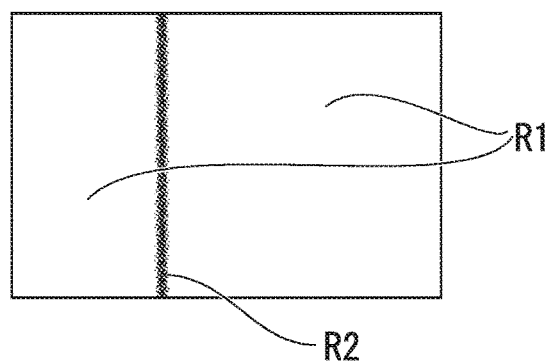
FIG. 9 is a schematic view showing a light and dark pattern projected by an endoscope apparatus of a modification according to the first embodiment of the present invention.

The shape of the light and dark pattern is not limited to the fringe pattern, and may be a plurality of linear parallel lines as shown in FIG. 2. Additionally, one line (to be described below) as shown in FIG. 9 may be provided as another example. Additionally, a grid-like pattern in which a plurality of points or a plurality of vertical lines and horizontal lines intersect each other, a concentric pattern, or the like may be adopted.

Other mechanisms provided within the body section 20 will be described. The first light source 41 and the second light source 51 are connected to a light source controller 21 that controls ON/OFF of the light sources. The imager controller 33, the pattern controller 56, and the light source controller 21 are connected to a main controller 22 that controls the entire endoscope apparatus 1. An operation section 23 that allows a user to perform various kinds of input to the endoscope apparatus 1 is connected to the main controller 22. Additionally, the main controller 22 is connected to a main storage device (RAM 24). In the present embodiment, an auxiliary storage device 25, such as a storage device having a rewritable nonvolatile memory or a magnetic storage device, is electrically connected to the main controller 22.

If necessary, a ROM 26 (or EPROM, EEPROM, or the like) on which firmware or the like is recorded may be connected to the main controller 22.

Moreover, the video processor 27 that processes video signals acquired by the imager 31 is connected to the imager controller 33 and the main controller 22. A monitor 28 that displays video signals processed by the video processor 27 as an image is connected to the video processor 27.

Next, the measuring method of the first embodiment of the present invention will be described through an example in which measurement is performed using the above-described endoscope apparatus 1.

The measuring method of the first embodiment of the present invention is a measuring method of performing the three-dimensional shape measurement of a subject, using the endoscope apparatus 1. When the endoscope apparatus 1 is used, first, a user inserts the insertion section 10 into the inside of the subject, an access path to the subject, such as a conduit, or the like, and advances the tip of the insertion section 10 to a predetermined observation region. The user performs inspection or the like of the subject by switching to an observation mode where a desired region of the subject is observed, and to a measurement mode where the three-dimensional shape of the region is measured, if necessary.

In the observation mode, the light source controller 21 receives the command from the main controller 22 to ON-control the first light source 41 and OFF-control the second light source 51. As a result, a fringe pattern is not projected from the pattern projection section 50 and white light is irradiated to the observation visual field from the illumination section 40 to illuminate the observation visual field (hereinafter, this illumination state is referred to as an "observation state"). The image of the illuminated subject is formed on the imager 31 through the objective optical system 32. Video signals sent from the imager 31 are processed by the video processor 27 and displayed on the monitor 28. The user can observe the subject from the image of the subject displayed on the monitor 28, or can save the image if necessary.

When switching is made from the observation mode to the measurement mode, the user inputs a mode switching instruction. A well-known input device can be used as an input device that inputs the mode switching instruction. For example, it is possible to adopt a configuration in which the operation section 23 is provided with a switch or a configuration in which the monitor 28 is changed to a touch panel so as to provide a software switch.

If the instructions to switch from the observation mode to the measurement mode are input by the user, measurement image capturing processing (refer to FIG. 3) is started in the main controller 22.

Figure 3:
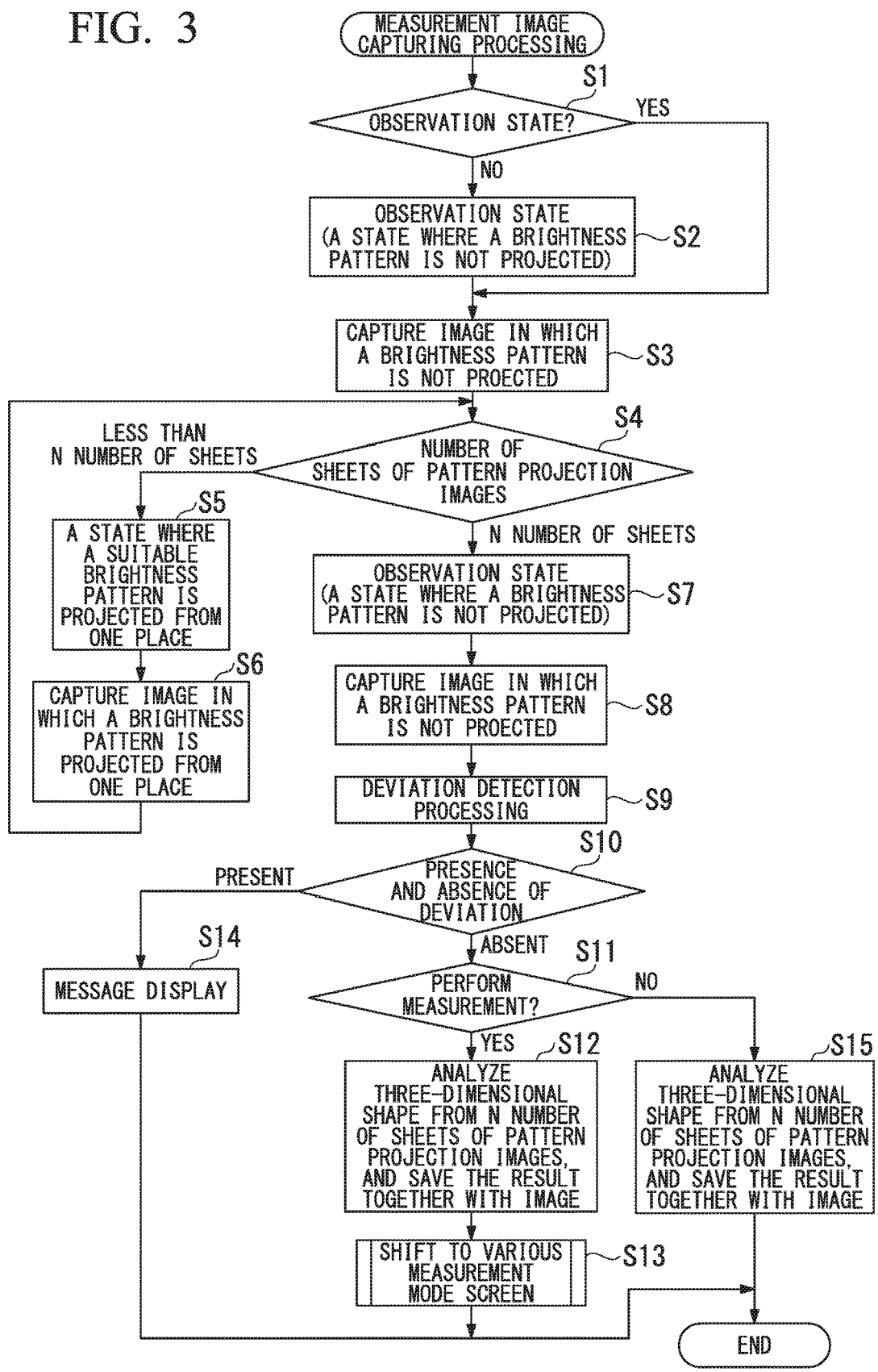
FIG. 3 is a flowchart showing a measuring method according to the first embodiment of the present invention.

In the measurement image capturing processing, first, it is determined whether or not the endoscope apparatus 1 has entered the observation state (Step S1 shown in FIG. 3).

When it is determined in Step S1 that the endoscope apparatus has entered the observation state, the processing proceeds to Step S3, and when the endoscope apparatus is in states (for example, a measurement state to be described below) excluding the observation state in Step S1, the processing proceeds to Step S2.

Step S1 is ended by this.

Step S2 is a step where the endoscope apparatus 1 is switched to being in the observation state.

In Step S2, the first light source 41 is ON-controlled, and the second light source 51 is OFF-controlled. Accordingly, a fringe pattern is not projected from the pattern projection section 50 and white light is irradiated to the observation visual field from the illumination section 40 to illuminate the observation visual field.

Step S2 is ended by this, and the processing proceeds to Step S3.

Step S3 is a step where a fringe pattern is not projected and the image of the subject illuminated with the white light from the illumination section 40 is captured.

In Step S3, an image is acquired by the imager 31 of the imaging section 30 in a state where the subject is illuminated with the white light from the illumination section 40 (hereinafter, the image captured in the observation state is referred to as a "bright field image").

The bright field image captured in Step S3 is temporarily stored in the RAM 24.

Step S3 is ended by this, and the processing proceeds to Step S4.

Step S4 is a branch step for capturing a desired number of sheets of pattern projection images.

In Step S4, a predetermined number N of sheets of pattern projection images scheduled to be captured is compared with the number of sheets of pattern projection images stored in the RAM 24 at this time. When the number of sheets of pattern projection images stored in the RAM 24 is less than the number N of sheets of images scheduled to be captured, the processing proceeds to Step S5. Additionally, when the number of sheets of pattern projection images stored in the RAM 24 is the number N of sheets of images scheduled to be captured, the processing proceeds to Step S7.

Step S4 is ended by this.

Step S5 is a step where a fringe pattern is projected onto the subject.

In Step S5, on the basis of the command from the main controller 22, the first light source 41 is OFF-controlled, and the second light source 51 is ON-controlled. Then, the white light irradiated from the illumination section 40 is turned off, and a fringe pattern is projected onto the subject from the pattern projection section 50. The fringe pattern projected onto the subject, as shown in FIG. 2, is a pattern in which a bright portion R1 by a white light source and a dark portion R2 shaded by the pattern generator 55 are alternately arranged. Additionally, the pattern generator 55 operates the actuator to set the phase of the fringe pattern to an appropriate phase. This is a state (hereinafter, this state is referred to as a "pattern projection state".) where an appropriate fringe is projected onto the subject from one place.

Step S5 is ended by this, and the processing proceeds to Step S6.

Step S6 is a step where a pattern projection image is captured in the pattern projection state.

In Step S6, the fringe pattern projected onto the subject is a pattern that has changed according to the three-dimensional shape of the subject. In this state, an image is acquired by the imager 31 of the imaging section 30 (hereinafter, the image captured in the pattern projection state is referred to as a "pattern projection image").

The pattern projection image captured in Step S6 is temporarily stored in the RAM 24.

Step S6 is ended by this, and the processing returns to Step S4.

Steps S4 to S6 are repeated until the number of sheets of pattern projection images to be captured reaches the number N of sheets of images scheduled to be captured. At this time, in Step S5, the phase of the fringe pattern is appropriately changed and the images of the subject on which fringes with different phases are projected are captured, for example, one by one by a total number N of sheets.

Step S7 is a step where the endoscope apparatus 1 is switched to being in the observation state.

In Step S7, the first light source 41 is ON-controlled, and the second light source 51 is OFF-controlled. Accordingly, a fringe pattern is not projected from the pattern projection section 50 and white light is irradiated to the observation visual field from the illumination section 40 to illuminate the observation visual field.

Step S7 is ended by this, and the processing proceeds to Step S8.

Step S8 is a step where a fringe pattern is not projected and the image of the subject illuminated with the white light from the illumination section 40 is captured.

In Step S8, a bright field image is captured by the imager 31 of the imaging section 30 in a state where the subject is illuminated with the white light from the illumination section 40.

The bright field image captured in Step S8 is temporarily stored in the RAM 24.

Step S8 is ended by this, and the processing proceeds to Step S9.

Step S9 is a step where the relative movement (hereinafter referred to as "deviation") between the insertion section 10 and the subject from Step S3 to Step S8 is detected on the basis of the images (the bright field image and the pattern projection image) captured from Step S3 to Step S8.

In Step S9, first, two sheets of images are selected from at least any of the bright field image and the fringe image that are stored in the RAM 24. For example, in the first embodiment, a bright field image captured before N sheets of pattern projection images are captured, and a bright field image captured after the N sheets of pattern projection images are captured are selected.

Subsequently, a same feature point is detected from the two sheets of selected images, and the coordinates of the feature point in the two sheets of images are calculated.

Step S9 is ended by this, and the processing proceeds to Step S10.

Step S10 is a step where a deviation of the two images is determined using the feature point detected in Step S9 and the processing branches.

In Step S10, if the coordinates of the feature point in the two sheets of images are the same coordinates in the respective images, it is determined that any deviation does not occur between a first image and the next image, and the processing proceeds to Step S11. On the contrary, if the coordinates of the feature point in the two sheets of images are different coordinates in the respective images, it is determined that deviation has occurred between the first image and the next image. Since the deviation has occurred, a message showing that another capturing is required is displayed on the monitor 28 (Step S14), and a series of processing is ended.

Step S10 is ended by this.

Step S11 is a step where the user is made to select whether three-dimensional measurement using the captured pattern projection image is performed at that time or later.

In Step S11, for example, an inquiry of "Perform measurement?" or the like is displayed on the monitor 28, and the user is urged to make an input on whether or not the three-dimensional measurement using the captured pattern projection image is allowed to be performed.

When there is an input that the measurement is allowed to be performed, the processing proceeds to Step S12.

When there is an input that the measurement is not allowed to be performed, the processing proceeds to Step S15.

Step S11 is ended by this.

Step S12 is a step where analysis is performed for the three-dimensional measurement.

In Step S12, the three-dimensional shape is analyzed on the basis of the pattern projection images stored in the RAM 24. For example, in the first embodiment, the three-dimensional shape of the subject is analyzed, for example, by the well-known time phase shift method, using the N sheets of pattern projection images with different phases.

The analysis result of the three-dimensional shape is generated as a text file or a binary file, and is saved together with the N sheets of pattern projection images in the auxiliary storage device 25. Step S12 may be performed as background processing during Step S11 simultaneously with the start of Step S11.

Step S12 is ended by this, and the processing proceeds to Step S13.

Step S13 is a step where the display on the monitor 28 is shifted to a screen of various measurement modes, and a measurement result is displayed on the monitor 28, using the information saved in Step S12.

In Step S13, the three-dimensional shape of the subject displayed on the bright field image is displayed on the monitor 28, by overlaying the result analyzed in Step S12 on the bright field image (or bright field image acquired in Step S8) acquired in Step S3. This enables the user to identify the three-dimensional shape of the subject.

Step S13 is ended by this, and a series of processing is ended.

Step S15 is a step that branches from the above Step S11, and is a step that performs information processing required to display the measurement result later.

In Step S15, similar to the above Step S12, the three-dimensional shape is analyzed on the basis of the pattern projection images stored in the RAM 24. For example, in the first embodiment, the three-dimensional shape of the subject is analyzed by the well-known time phase shift method, using the N sheets of pattern projection images with different phases.

Additionally, analysis results of the bright field image, the pattern projection image, and the three-dimensional shape and optical parameters used for the analysis are saved as binary files or text files, respectively, in the auxiliary storage device 25. In this case, by making portions of file names common or collectively saving these files in one directory (folder), these files are saved in the auxiliary storage device 25 so that the files can be collectively read later.

Step S15 is ended by this, and a series of processing is ended.

As described above, according to the endoscope apparatus 1 of the first embodiment of the invention, the projection window 13 of the pattern projection section 50 is provided in one place of the tip surface 10a of the insertion section 10. Thus, the diameter of the insertion section 10 can be reduced as compared to a case where two projection windows 13 are provided in the tip surface 10a of the insertion section 10.

Additionally, if projection windows 13 used for projecting a fringe pattern are provided in a plurality of places as in the related art, the occupying area of the projection window 13 in the tip surface 10a of the insertion section 10 of the endoscope apparatus 1 is large, and the occupying area of the illumination window 12 and the objective optical system 32 is difficult to increase. For example, if the occupying area of the illumination window 12 is small, the quantity of illumination light may be insufficient. Additionally, if the occupying area of the objective optical system 32 is small, it may be difficult to increase the aperture of a lens, and an image may become dark.

In contrast, in the endoscope apparatus 1 of the first embodiment of the present invention, the number of projection windows 13 through which a fringe pattern is projected is one. Thus, the occupying area of the illumination window 12 or the objective optical system 32 is capable of being increased. As a result, a brighter image can be acquired even in the insertion section 10 with a thickness equal to that of the endoscope according to related art. Additionally, even in the insertion section 10 whose diameter is reduced compared to the related-art endoscope, an image with a brightness equal to or higher than that of the endoscope according to related art is capable of being obtained.

According to the measuring method of the first embodiment of the present invention, even in an environment where a fringe pattern is projected from one projection window 13 in the endoscope apparatus 1 in which the diameter of the insertion section 10 is reduced, a three-dimensional shape can be measured with high precision.

According to the measuring method of the first embodiment of the present invention, deviation is detected using bright field images before and after a pattern projection image is captured, and a three-dimensional shape is analyzed when it is determined that there is no deviation. Thus, analysis is not performed with fringe patterns on a plurality of pattern projection images deviated. For this reason, the analysis precision of the three-dimensional shape can be enhanced. Moreover, when the measurement result by using the pattern projection image is overlaid on the bright field images and displayed, the positional deviations are capable of being reduced.

Modification 1 of the First Embodiment

Next, a modification 1 of the endoscope apparatus 1 and the measuring method according to the above-described first embodiment will be described.

The present modification 1 is different from the above-described first embodiment that the present modification 1 includes a pattern generator 55A (refer to FIG. 1) instead of the pattern generator 55. The pattern generator 55A is not capable of projecting light and dark patterns with different phases. However, the pattern generator 55A is configured so that a light and dark pattern with a specific phase can be projected onto a subject. That is, the pattern generator 55A of the present modification 1 does not include an actuator that moves the slit plate or the like, and is configured of a small size.

In the present modification 1, a measuring method of the three-dimensional shape measurement of a subject is also different. The measuring method of the present modification 1 will be described below mainly about points that are different from the above-described first embodiment in terms of processing.

In the measuring method of the present modification 1, the number N of sheets of images scheduled to be captured in Step S4 is 1, one sheet of a pattern projection image is captured without any repetition from Step S4 to Step S6 in the above-described embodiment, and the processing proceeds to Step S7.

Additionally, the analysis method of a three-dimensional shape measurement in Step S12 and Step S15 are also different from that of the above-described first embodiment. In the present modification 1, the three-dimensional shape is analyzed by a space phase shift method or a Fourier transform method in Step S12 and Step S15 using one sheet of a pattern projection image.

In the present modification 1, the three-dimensional shape is analyzed using one sheet of the pattern projection image.

Thus, as compared to the case where N sheets of fringe images are acquired in the above-described first embodiment, the time until an analysis result is obtained after capturing of an image is started can be shortened.

The measuring method of the present modification 1 is a similarly applicable method even if the method has the pattern generator 55 including the actuator that moves the slit plate or the like, and can rapidly analyze a three-dimensional shape compared to the time phase shift method using a plurality of sheets of pattern projection images.

Modification 2 of the First Embodiment

Next, a modification 2 of the endoscope apparatus 1 and the measuring method according to the above-described first embodiment will be described.

The present modification 2 includes the pattern generator 55A (refer to FIG. 1), and the pattern projection section 50 is configured so that the pattern projection section is capable of projecting one light or dark linear pattern as shown in FIG. 9 onto a subject. A case where a stripe-shaped (straight) dark portion R2 is projected into a light portion R1 is shown in FIG. 9. In addition, one stripe-shaped light portion R1 may be projected into the dark portion R2.

The pattern itself projected from the pattern projection section 50 is not moved in terms of projection place or direction or is not deformed in terms of shape.

That is, the pattern generator 55A of the present modification 2 does not include the actuator that moves the slit plate or the like, and is configured with a small size.

In the present modification 2, the measuring method of the three-dimensional shape measurement of a subject is also different. The measuring method of the present modification 2 will be described below mainly about the point that the present modification 2 is different from Modification 1 of the first embodiment as described above in terms of processing.

In the present modification 2, the three-dimensional shape is analyzed in Step S12 and Step S15 by an optical cutting method, using one sheet of a pattern projection image. In the present modification 2, the three-dimensional shape is analyzed on one pattern, using one sheet of a pattern projection image. Therefore, as compared to the case where the entire surface of one sheet of a pattern projection image is analyzed in the above-described first embodiment, a portion where the three-dimensional shape measurement is capable of being performed is limited, but analysis time can be significantly shortened.

The measuring method of the present modification 2 is a similarly applicable method even if the pattern generator 55 includes the actuator that moves the slit plate or the like. By using a plurality of sheets of pattern projection images, the three-dimensional shape can be rapidly analyzed not only in a portion of a visual field range (on the screen) but also in a plurality of different portions (positions).

Modification 3 of the First Embodiment

Next, a modification 3 of the endoscope apparatus 1 according to the above-described first embodiment will be described.

The present modification 3 does not include the second light source 51, but includes switching means that makes the light emitted from the first light source 41 incidents on the second fiber bundle 53.

As the switching means, for example, devices, such as a MEMS mirror module, which switch an optical path for the light emitted from the first light source 41 to a plurality of directions, can be adopted.

Even in such a configuration, the same effects as the endoscope apparatus 1 described in the above-described first embodiment are exhibited. Additionally, since the light source may be comprised of one light source, the number of parts of the endoscope apparatus 1 is capable of being reduced.

Modification 4 of the First Embodiment

Next, a modification 4 of the endoscope apparatus 1 according to the above-described first embodiment will be described.

In the present modification 4, the configuration of the tip surface 10a of the endoscope apparatus 1 is different from that of the above-described first embodiment.

Figure 4:
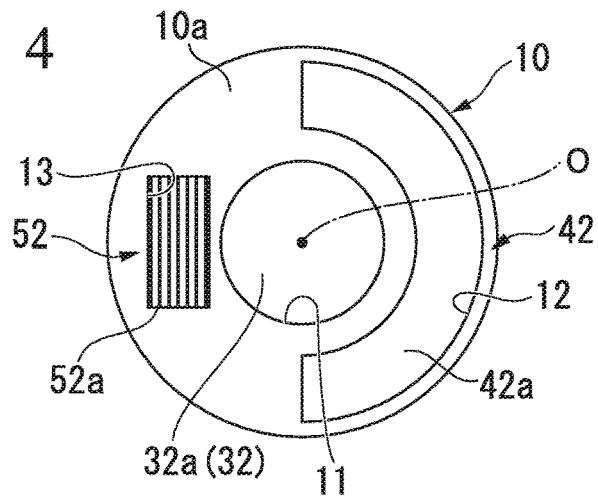
FIG. 4 is a schematic view showing a first example of the configuration of a tip surface of an insertion section of the endoscope apparatus according to the first embodiment of the present invention.
Figure 5:
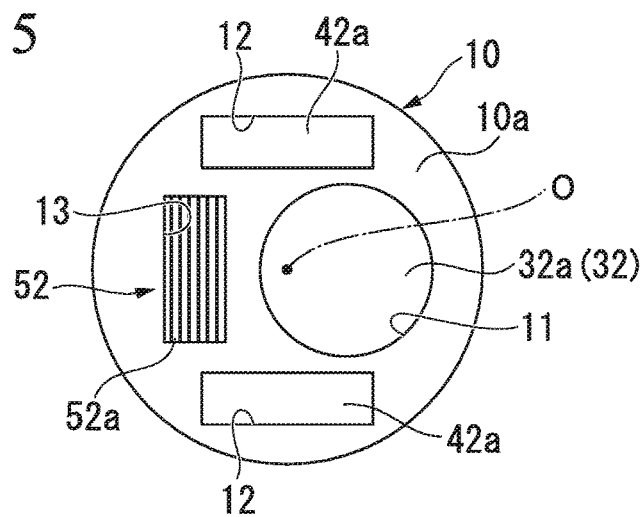
FIG. 5 is a schematic view showing a second example of the configuration of the tip surface of the insertion section of the endoscope apparatus according to the first embodiment of the present invention.
Figure 6:
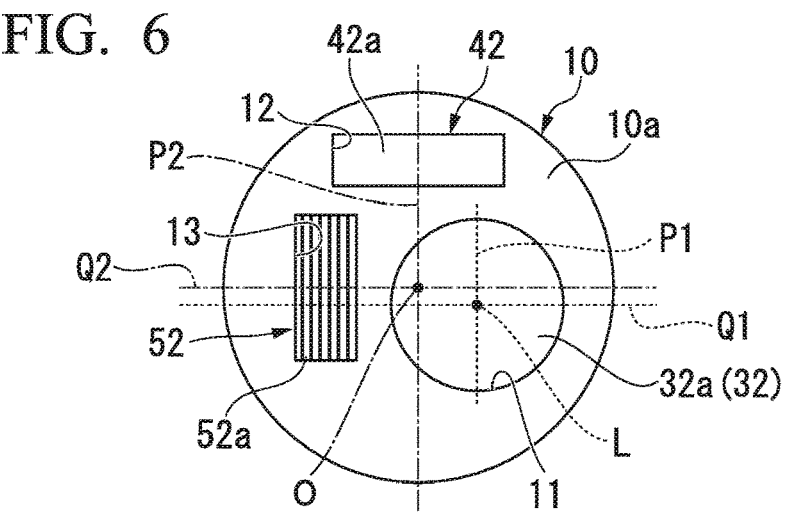
FIG. 6 is a schematic view showing a third example of the configuration of the tip surface of the insertion section of the endoscope apparatus according to the first embodiment of the present invention.

FIGS. 4 to 6 are views showing the configuration of the direct-view-type insertion section 10 including the illumination window 12, the projection window 13, and the like in the tip surface 10a.

As shown in FIGS. 4 to 6, there are various embodiments in the configuration of respective elements in the tip surface 10a of the insertion section 10 of the endoscope apparatus 1.

For example, as shown in FIG. 4, the objective optical system 32 is arranged on a central axis O of the insertion section 10. The illumination window 12 is provided so as to surround the objective optical system 32 by a half of an outer periphery of the objective optical system 32. The projection window 13 is arranged opposite to the objective optical system 32 with respect to the illumination window 12. In such an arrangement, the occupying area of the illumination window 12 is capable of being increased. Additionally, the shape of the objective optical system 32 is generally a circle or a shape close to a circle. Therefore, by arranging the illumination window 12 and the projection window 13 around the objective optical system 32, the illumination window and the projection window can be efficiently arranged at the tip portion of the endoscope with limited arrangement area, and the diameter of the tip portion of an endoscope is easily reduced. Moreover, since the center of an endoscope image and the central axis O of the insertion section 10 coincide with each other, an operator can insert the endoscope without a sense of incompatibility while observing the image of a subject by the monitor.

The pattern generator 55 is provided on the depth side of the projection window 13. The pattern generator 55 is arranged so that a linear pattern is located in a vertical direction with respect to the arrangement direction of the projection window 13 and the objective optical system. Such an arrangement secures the distance (hereinafter referred to as a base length) perpendicular to the linear pattern from the central point of the objective optical system as long as possible, and constitutes an arrangement relationship in which the arrangement interval between the projection window and the objective optical system is the closest. Since measurement precision improves as the base length is longer, according to the present modification example, the three-dimensional shape can be measured with high precision even in the endoscope apparatus in which the diameter of the insertion section is reduced.

As shown in FIG. 5, the objective optical system 32 is arranged at a position eccentric from the central axis O of the insertion section 10 unlike the arrangement shown in FIG. 4. As shown in FIG. 5, it is also possible to provide an arrangement in which the illumination windows 12 are provided in two places between which the objective optical system 32 and the projection window 13 are sandwiched. The objective optical system 32 is arranged so that an optical axis on the emission side where the reflected light within the observation visual field is directed to the imager 31 from the objective optical system 32 is parallel to and eccentric from the central axis O.

As shown in FIG. 6, in the tip surface 10a of the insertion section 10, the opening 11 in which the objective optical system 32 is arranged, the illumination window 12, and the projection window 13 may be arranged at positions eccentric from the central axis O of the insertion section 10. Additionally, a vertical axis P1 and a left-right axis Q1 that pass through the optical axis L of the objective optical system 32 may be arranged at positions where these axes do not overlap a vertical axis P2 and a left-right axis Q2 that pass through the central axis of the insertion section 10.

Since the opening 11, the illumination window 12, and the projection window 13 are provided at the positions eccentric from the central axis O of the insertion section 10, the diameter of the insertion section 10 can be further reduced, for example, as compared to a related-art endoscope apparatus in which the objective optical system 32 is provided on the central axis O of the insertion section 10.

Modification 5 of the First Embodiment

Next, a modification 5 of the endoscope apparatus 1 according to the above-described first embodiment will be described.

In the present modification 5, the first light source 41 and the second light source 51 are arranged in the vicinity of the tip of the insertion section 10.

Figure 7:
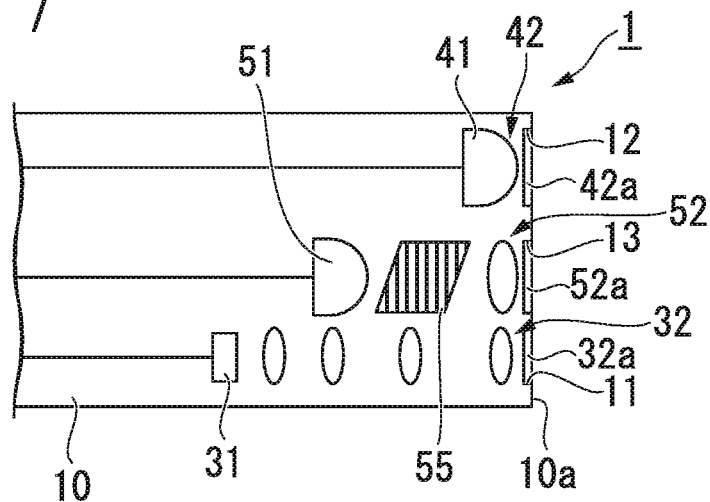
FIG. 7 is a schematic view showing a first example of a configuration in the vicinity of the tip of the insertion section of the endoscope apparatus according to the first embodiment of the present invention.

For example, as shown in FIG. 7, in the present modification 5, the first fiber bundle 43 is not included, the light from the first light source 41 is directly irradiated toward the illumination window 12, the second fiber bundle 53 is not included, and the light from the second light source 51 is directly irradiated toward the fringe pattern generator 55.

Figure 8:
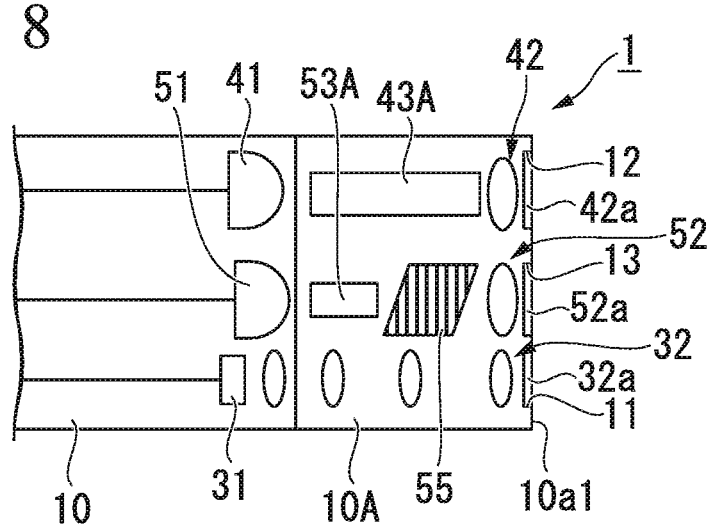
FIG. 8 is a schematic view showing a second example of the configuration in the vicinity of the tip of the insertion section of the endoscope apparatus according to the first embodiment of the present invention.

As shown in FIG. 8, it is also possible to adopt a configuration having the first light source 41, the second light source 51, and the imager 31 in the vicinity of the tip of the insertion section 10 and having an optical adapter 10A that is attachable to and detachable from a tip portion of the insertion section 10.

Portions of the illumination window 12, the projection window 13, and the objective optical system 32 are accommodated in the optical adapter 10A. Additionally, a tip surface 10a1 of the optical adapter 10A corresponds to the tip surface 10a of the insertion section 10 in the above-described first embodiment.

The first light source 41 and the illumination window 12 are connected together by an optical fiber 43A arranged within the optical adapter 10A. Additionally, the second light source 51 and the pattern generator 55 are connected together by an optical fiber 53A arranged within the optical adapter 10A.

Even in configurations as shown in FIGS. 7 and 8, the same effects as those described in the above-described first embodiment are exhibited.

Since the first light source 41 and the second light source 51 are provided in the vicinity of the tip of the insertion section 10, when the insertion section 10 has, for example, a length exceeding several tens of meters, there is little loss of light and a brighter image is capable of being acquired, compared to a case where the first fiber bundle 43 and the second fiber bundle 53 are used.

Modification 6 of the First Embodiment

Next, a modification 6 of the endoscope apparatus 1 according to the above-described first embodiment will be described.

Figure 10:
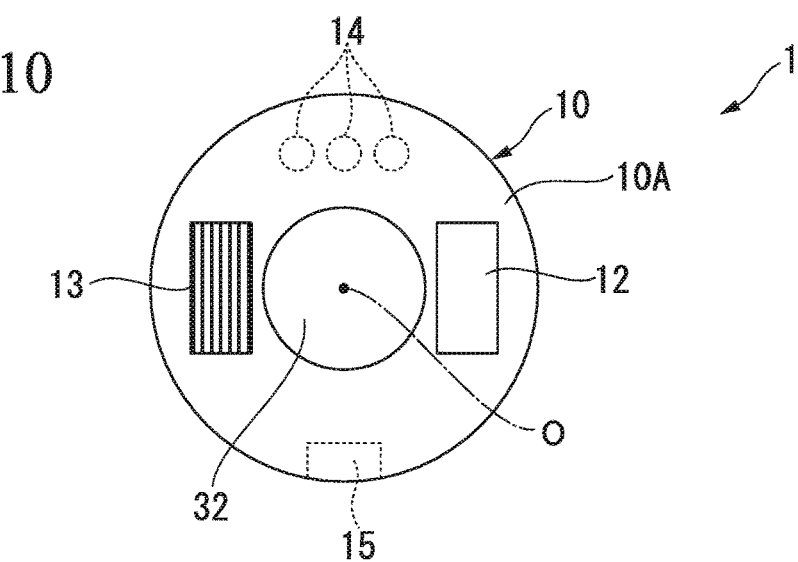
FIG. 10 is a schematic view showing the configuration of a tip surface of an insertion section in another modification of the endoscope apparatus according to the first embodiment of the present invention.

FIG. 10 shows a modification of another arrangement in which the arrangement of FIG. 6 is further modified. This modification is an example of the endoscope apparatus of a configuration having the optical adapter 10A. FIG. 10 shows a view of the tip surface of the optical adapter.

The objective optical system 32 is arranged on the central axis O of the insertion section 10, and the illumination window 12 and the projection window 13 are respectively arranged on both sides of the objective optical system 32. Contact pins 14 used to supply electric power to the first light source or the second light source from the body are provided on the back of the optical adapter 10A.

When the optical adapter 10A is attached to the tip portion of the insertion section 10, in order to perform positioning in the rotational direction to the central axis of the insertion section, a positioning groove 15 or a structure in place of the positioning groove is provided on the back of the optical adapter 10A.

Such contact pins 14 and positioning groove 15 are respectively provided on sides where the illumination window 12 and the projection window 13 are not arranged, with respect to the objective optical system 32. This allows the contact pins 14, the positioning groove 15, the illumination window 12, and the projection window 13 to be arranged in a small-diameter endoscope tip portion without interfering with each other, even in an optical adapter type.

Modification 7 of the First Embodiment

Next, a modification 7 of the endoscope apparatus 1 according to the above-described first embodiment will be described.

Figure 11:
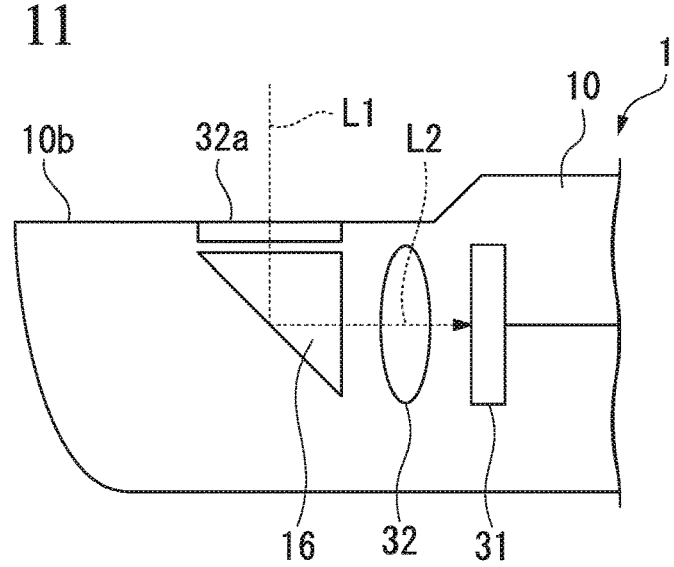
FIG. 11 is a view showing the configuration of an insertion section in a still further modification of the endoscope apparatus according to the first embodiment of the present invention, and a schematic view of the insertion section in the endoscope apparatus capable of being observed in a vertical direction with respect to the central axis of the insertion section.

FIG. 11 shows the modification 7 of the tip portion in the endoscope apparatus capable of performing observation in a perpendicular direction to the central axis of the insertion section.

In the present modification 7, in place of the tip surface 10a, a tip surface 10b in which a straight line orthogonal to the central axis of the insertion section 10 becomes a normal line is formed in a portion of an outer peripheral surface of the tip portion of the insertion section 10. The illumination window 12, the projection window 13, and the cover member 32a are all arranged at the tip surface 10b.

The objective optical system 32 has a prism 16 in which an optical axis L1 on the incidence side is directed to a direction that intersects the optical axis L2 on the emission side that turns from the objective optical system 32 to the imager 31. In the present modification 7, the prism 16 is one of optical elements that configure the objective optical system 32.

The optical axis L1 on the incidence side is an optical axis when the reflected light within the observation visual field is incident on the prism 16, and the optical axis L2 on the emission side is an optical axis when the reflected light within the observation visual field is incident on the imager 31 from the prism 16.

In the present modification 7, the optical axis L1 on the incidence side is at a twisted position with respect to the central axis O of the insertion section 10. Moreover, the optical axis L2 on the emission side is parallel to the central axis O of the insertion section 10.

Figure 12A:
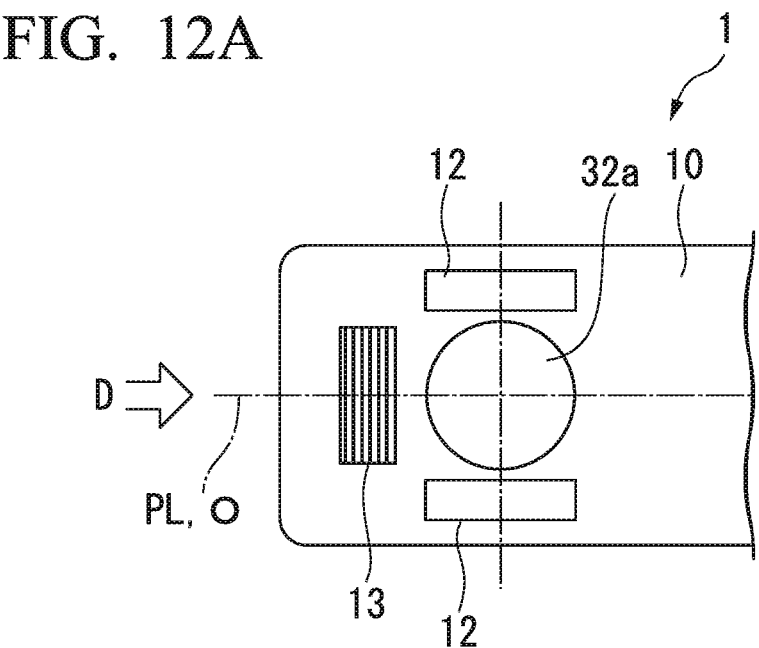
FIG. 12A is a top view of a tip surface on which a cover member of a prism according to the modification shown in FIG. 11 is put.
Figure 12B:
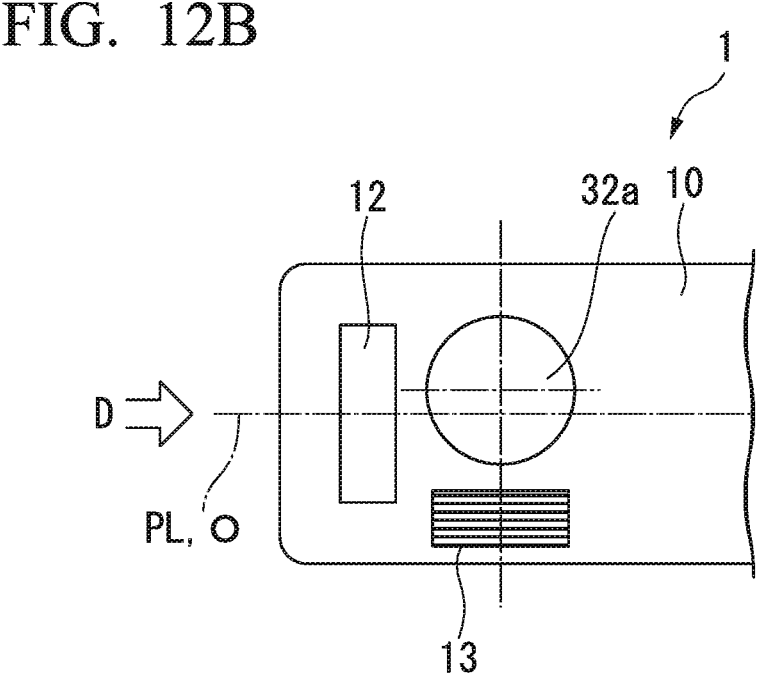
FIG. 12B is a top view of a tip surface on which the cover member of the prism according to the modification shown in FIG. 11 is put.

FIG. 12A and FIG. 12B are views of the tip surface 10b in the endoscope of FIG. 11 as viewed from a direction perpendicular to the tip surface 10b, and are plan views showing an arrangement example of the illumination window 12, the projection window 13, and the cover member 32a.

As shown in FIGS. 11 and 12A, the tip surface 10b is a substantially flat plane. As shown in FIG. 12A, in the present modification, the cover member 32a and the projection window 13 are arranged on the central axis O of the insertion section 10 in plan view. Two illumination windows 12 are arranged on the sides of the cover member 32a. Both the cover member 32a and the projection window 13 are exposed to the tip surface 10b that is the outer peripheral surface of the tip portion of the insertion section. In the present modification 7, a line obtained by projecting the central axis O perpendicularly to the tip surface 10b is defined as a virtual centerline PL. That is, in FIG. 12A, the cover member 32a and the projection window 13 are arranged at positions where the centers of these and the virtual centerline PL intersect each other. In this case, the projection window 13 has a positional relationship in which the center of the projection window when the projection window 13 is viewed from the thickness direction of the projection window 13 is present within a plane defined by the central axis O of the insertion section 10 and the optical axis L1 on the incidence side.

As shown in FIG. 12B, the cover member 32a may be arranged at a position where the center thereof does not intersect the virtual centerline PL, the illumination window 12 may be arranged on the virtual centerline PL of the insertion section 10, and the projection window 13 may be arranged at a position where the center thereof does not intersect the virtual centerline PL.

At this time, the center of the cover member 32a and the optical axis L1 of the prism 16 are arranged so as to coincide with each other, and the objective optical system 32 is arranged so that the optical axis L1 thereof does not intersect the virtual centerline PL.

Figure 12C:
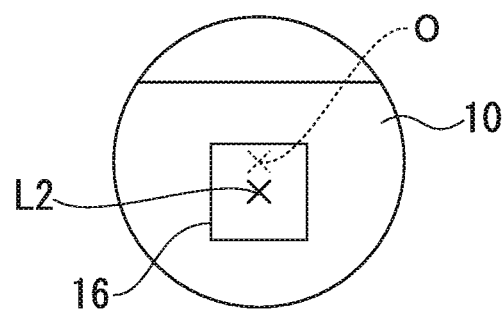
FIG. 12C is a schematic view of the modification shown in FIG. 12A as viewed from a direction D.
Figure 12D:
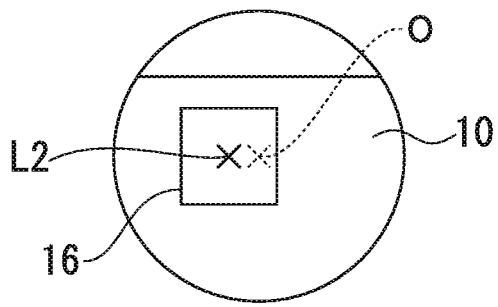
FIG. 12D is a schematic view of the modification example shown in FIG. 12B as viewed from the direction D.

FIG. 12C and FIG. 12D are respectively schematic views of the insertion section 10 as viewed from a direction shown by symbol D in FIG. 12A and FIG. 12B, and are front views of the insertion section 10. As shown in FIG. 12C and FIG. 12D, in the present modification 7, the objective optical system 32 and the imager 31 are arranged so that the optical axis L2 when the reflected light within the observation visual field is incident on the imager 31 from the prism 16 and the central axis O of the insertion section 10 are eccentric from each other.

As shown in FIG. 11 and FIG. 12A to FIG. 12D, even in the example of the endoscope that performs observation in the lateral direction, the diameter of the tip portion is easily reduced because the number of projection windows is one, compared to the case where projection windows 13 used for projecting a light and dark pattern are provided in a plurality of places as in the related art.

The shapes and arrangement positions of the respective elements arranged at the tip surface are not limited only to the examples of FIG. 12A and FIG. 12B. For example, although the case where the optical axis L1 and the optical axis L2 are orthogonal to each other is illustrated in the present modification example, a configuration in which the optical axis L1 and the optical axis L2 intersect each other at angles other than the orthogonal intersection.

Modification 8 of the First Embodiment

Next, a modification example 8 of the endoscope apparatus 1 described in the above-described first embodiment will be described.

In the present modification example, the control operation performed by the main controller 22 is different from those of the above-described first embodiment and Modifications 1 to 7 of the first embodiment.

In the present modification 8, the second light source 51, as shown in FIG. 7, is provided on the tip side of the insertion section 10, and is, for example, a high-luminance light source, such as a laser. In this case, in Step S5, a state where a suitable fringe is projected onto a subject from one place may enter a "fringe projection state" by ON-controlling the second light source 51 with the first light source 41 being ON-controlled, on the basis of the command of the main controller 22. Additionally, when captured images are nth and (n+1)th in the above-described Step S5, fringe images with different fringe luminance may be captured by controlling the second light source 51 to thereby change the quantity of light, without changing the phase of a light and dark pattern.

Modification 9 of the First Embodiment

Next, a modification 9 of the endoscope apparatus 1 described in the above-described first embodiment will be described.

In the present modification 9, the control operation performed by the main controller 22 is different from those of the above-described first embodiment and Modifications 1 to 8 of the first embodiment.

In the present modification example, in the above-described Step S9, a bright field image captured before N sheets of fringe images are captured, and a bright field image captured after the N sheets of fringe images are captured are selected, and the total differences in luminance value between the two sheets of images is calculated.

Moreover, in the above-described Step S10, if the total of the differences in luminance value calculated in Step S9 is smaller than a threshold, it is determined that any deviation does not occur in a first image and the next image, and the processing proceeds to Step S11. On the contrary, when the total of the differences in luminance value calculated in Step S9 is larger than the threshold, it is determined that deviation has occurred in the first image and the next image. Since the deviation has occurred, a message showing that another capturing is required is displayed on the monitor 28 (Step S14), and a series of processing is ended.

The above example is an example in which differences are calculated all over an image. In addition, processing may be performed using only a certain portion of an image as an object. Additionally, differences in luminance may be calculated using one sheet of a bright field image and one sheet of a fringe image.

Modification 10 of the First Embodiment

Next, a still further modification example of the endoscope apparatus 1 described in the above-described first embodiment will be described.

In the present modification 10, the control operation performed by the main controller 22 is different from those of the above-described first embodiment and Modifications 1 to 9.

In the present modification 10, the second light source 51 (refer to FIG. 7) is configured by a plurality of minute light-emitting elements. The plurality of light-emitting elements provided in the second light source 51 is lighting-controlled every two or more groups.

For example, a plurality of groups based on the light-emitting elements may be a plate with simple slits in which the light and dark pattern generator 55 cannot arbitrarily change the phase of a fringe, or a plate similar thereto, if the groups are arranged in the phase direction of a fringe pattern provided on the light and dark pattern generator 55. In this case, in Step S5, a plurality of several different fringes are projected onto the subject by switching groups of light-emitting elements to be turned on in order. Moreover, these respective fringe images can be captured in Step S6.

Although the first embodiment of the invention has been described above in detail with reference to the drawings, specific configuration is not limited to the embodiment, and design changes are also included without departing from the scope of the invention.

For example, although the example in which the two sheets of bright field images are selected as the images to be used in order to detect any deviation is shown in the above-described first embodiment, fringe images may be used as the images to be used in order to detect any deviation. Additionally, bright field images more than two sheets of images may be captured. If there are bright field images more than two sheets of images, any deviation can be detected by selecting a required number of sheets of images from the bright field images if necessary.

Additionally, the elements shown in the above-described first embodiment and respective modifications can be suitably combined.

Second Embodiment

A measuring method of a second embodiment of the invention will be described below.

The measuring method of the present embodiment is a method of performing the three-dimensional shape measurement of a subject, using an endoscope apparatus.

First, the configuration of the endoscope apparatus 1 to which the measuring method of the present embodiment is applied will be described. FIG. 1 is a block diagram showing the configuration of the endoscope apparatus 1 of the present embodiment. FIG. 2 is a schematic view showing a light and dark pattern projected by the endoscope apparatus 1.

The configuration of the endoscope apparatus of the second embodiment is the same as the configuration of the endoscope apparatus of the first embodiment. Accordingly, the same elements as those of the first embodiment will be designated by the same reference numerals, and a detailed description thereof will be omitted here.

Next, the measuring method of the second embodiment of the present invention will be described through an example in which measurement is performed using the above-described endoscope apparatus 1.

Similar to the first embodiment, in the second embodiment, when the endoscope apparatus 1 is used, first, a user inserts the insertion section 10 into the inside of a subject, an access path to the subject, such as a conduit, or the like, and advances the tip of the insertion section 10 to a predetermined observation region. The user performs inspection or the like of the subject by switching to an observation mode where a desired region of the subject is observed and a measurement mode where the three-dimensional shape measurement of the region is performed, if necessary.

In the observation mode, the light source controller 21 receives the command of the main controller 22 to ON-control the first light source 41 and OFF-control the second light source 51. As a result, a fringe pattern is not projected from the pattern projection section 50 and white light is irradiated to the observation visual field from the illumination section 40 to illuminate the observation visual field (hereinafter, this illumination state is referred to as an "observation state"). The image of the illuminated subject is formed on the imager 31 through the objective optical system 32. Video signals sent from the imager 31 are processed by the video processor 27 and displayed on the monitor 28. The user can observe the subject from the image of the subject displayed on the monitor 28, or save the image if necessary.

When switching is made from the observation mode to the measurement mode, the user inputs a mode switching instruction. A well-known input device can be used as an input device on which the mode switching instruction is input. For example, it is possible to adopt a configuration in which the operation section 23 is provided with a switch or a configuration in which the monitor 28 is changed to a touch panel so as to provide a software switch.

If a mode switching instruction from the observation mode to the measurement mode is input by the user, measurement image capturing processing (refer to FIG. 13) is started in the main controller 22.

Figure 13:
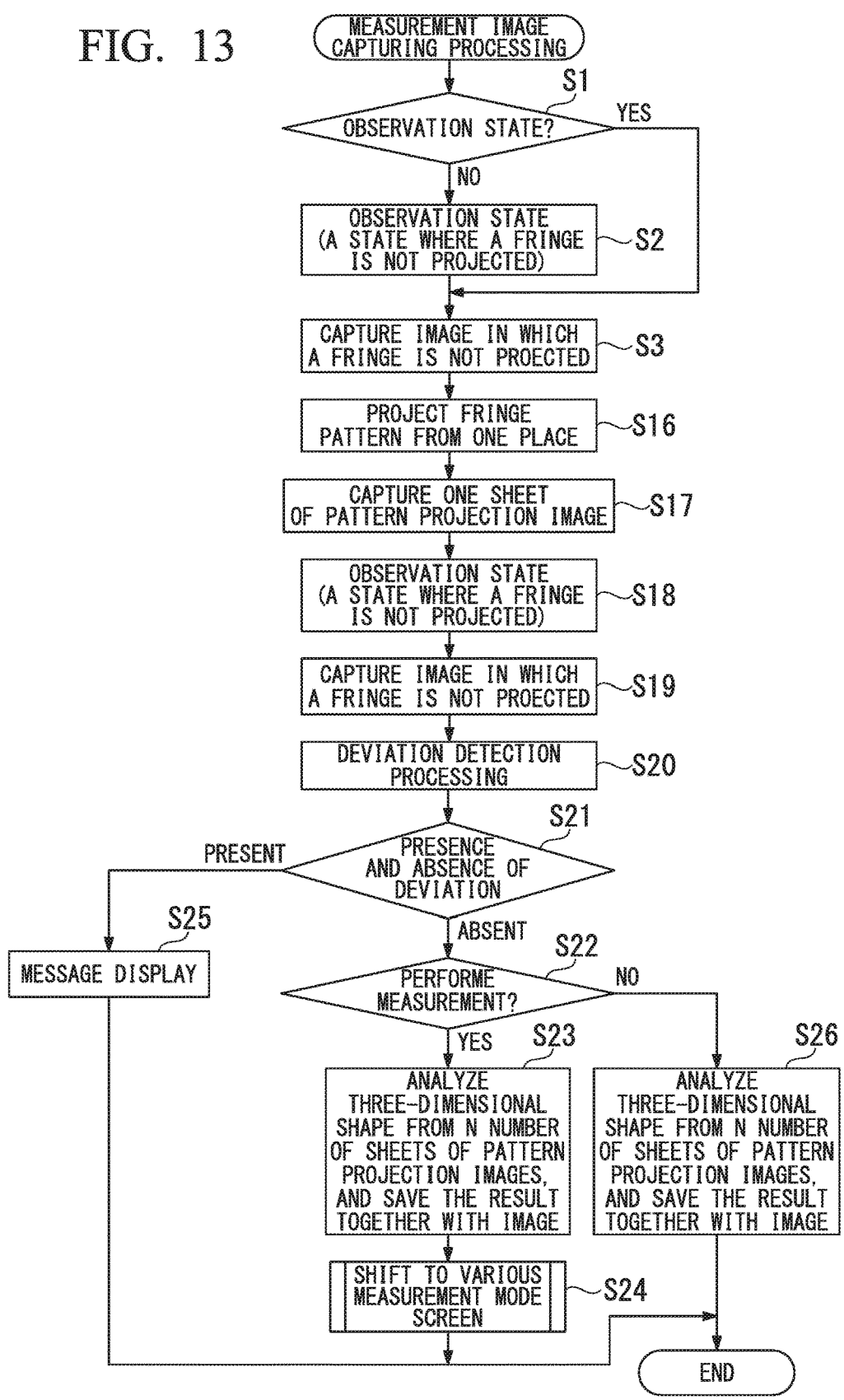
FIG. 13 is a flowchart showing a measuring method according to the second embodiment of the invention.

In the measurement image capturing processing, first, it is determined whether or not the endoscope apparatus 1 is brought into the observation state (Step S1 shown in FIG. 13).

When it is determined in Step S1 that the endoscope apparatus has been brought into the observation state, the processing proceeds to Step S3, and when the endoscope apparatus is brought into states (for example, a measurement state to be described below) excluding the observation state in Step S1, the processing proceeds to Step S2.

Step S1 is ended by this.

Step S2 is a step where the endoscope apparatus 1 is switched to being in the observation state.

In Step S2, the first light source 41 is ON-controlled, and the second light source 51 is OFF-controlled. Accordingly, a fringe pattern is not projected from the pattern projection section 50 and white light is irradiated to the observation visual field from the illumination section 40 to illuminate the observation visual field.

Step S2 is ended by this, and the processing proceeds to Step S3.

Step S3 is a step where a fringe pattern is not projected and the image of the subject illuminated with the white light from the illumination section 40 is captured.

In Step S3, an image is acquired by the imager 31 of the imaging section 30 in a state where the subject is illuminated with the white light from the illumination section 40 (hereinafter, the image captured in the observation state is referred to as a "bright field image").

The bright field image captured in Step S3 is temporarily stored in the RAM 24.

Step S3 is ended by this, and the processing proceeds to Step S16.

Step S16 is a step where a predetermined fringe pattern is projected onto the subject from one place of the endoscope apparatus 1.

In Step S16, on the basis of the command of the main controller 22, the first light source 41 is OFF-controlled, and the second light source 51 is ON-controlled. Then, the white light irradiated from the illumination section 40 is turned off, and a fringe pattern is projected onto the subject from the pattern projection section 50. The fringe pattern projected onto the subject, as shown in FIG. 2, is a pattern in which a light portion R1 by a white light source and a dark portion R2 shaded by the pattern generator 55 are alternately arranged. (Hereinafter, this state is referred to as a "pattern projection state").

Step S16 is ended by this, and the processing proceeds to Step S17.

Step S17 is a step where a pattern projection image is captured in the pattern projection state.

In Step S17, the fringe pattern projected onto the subject is a pattern that has changed according to the three-dimensional shape of the subject. In this state, one sheet of an image is acquired by the imager 31 of the imaging section 30 (hereinafter, the image captured in the pattern projection state is referred to as a "pattern projection image").

The pattern projection image captured in Step S17 is temporarily stored in the RAM 24.

Step S17 is ended by this, and the processing proceeds to Step S18.

Step S18 is a step where the endoscope apparatus 1 is switched to being in the observation state.

In Step S18, the first light source 41 is ON-controlled, and the second light source 51 is OFF-controlled. Accordingly, a fringe pattern is not projected from the pattern projection section 50 and white light is irradiated to the observation visual field from the illumination section 40 to illuminate the observation visual field.

Step S18 is ended by this, and the processing proceeds to Step S19.

Step S19 is a step where a fringe pattern is not projected and the image of the subject illuminated with white light from the illumination section 40 is captured.

In Step S19, a bright field image is acquired by the imager 31 of the imaging section 30 in a state where the subject is illuminated with white light from the illumination section 40.

The bright field image captured in Step S19 is temporarily stored in the RAM 24.

Step S19 is ended by this, and the processing proceeds to Step S20.

Step S20 is a step where the relative movement (hereinafter referred to as "deviation") between the insertion section 10 and the subject from Step S3 to Step S19 is detected on the basis of the images (the bright field image and the pattern projection image) captured from Step S3 to Step S19.

In Step S20, first, two sheets of images are selected from at least any of the bright field image and the pattern projection image that are stored in the RAM 24. For example, in the second embodiment, a bright field image captured before one sheet of a pattern projection image is captured, and a bright field image captured after the one sheet of pattern projection image is captured are selected.

Subsequently, the same feature point is detected from the two sheets of selected images, and the coordinates of the feature point in the two sheets of images are calculated.

Step S20 is ended by this, and the processing proceeds to Step S21.

Step S21 is a step where the deviation of the two images is determined using the feature point detected in Step S20 and the processing branches.

In Step S21, if the coordinates of the feature point in the two sheets of images are the same coordinates in the respective images, it is determined that no deviation occurs between a first image and the next image, and the processing proceeds to Step S22. On the contrary, if the coordinates of the feature point in the two sheets of images are different coordinates in the respective images, it is determined that deviation has occurred between the first image and the next image. Since the deviation has occurred, a message showing that another capturing is required is displayed on the monitor 28 (Step S25), and a series of processing is ended.

Step S21 is ended by this.

Step S22 is a step where the user is made to select whether three-dimensional measurement using the captured pattern projection image is performed now or later.

In Step S22, for example, an inquiry of "Perform measurement?" or the like is displayed on the monitor 28, and the user is urged to make an input on whether or not the three-dimensional measurement using the captured pattern projection image is performed.

When there is an input that the measurement is capable of being performed, the processing proceeds to Step S23.

When there is an input that the measurement is not capable of being performed, the processing proceeds to Step S26.

Step S22 is ended by this.

Step S23 is a step where analysis is performed for the three-dimensional measurement.

In Step S23, the three-dimensional shape is analyzed on the basis of the pattern projection images stored in the RAM 24. For example, in the second embodiment, the three-dimensional shape of the subject is analyzed, for example, by the well-known spatial phase shift method or Fourier transform method, using one sheet of a pattern projection image.

The analysis result of the three-dimensional shape is generated as a text file or a binary file, and is saved together with the pattern projection image in the auxiliary storage device 25. In addition, Step S23 may be performed as background processing of Step S22 simultaneously with the start of Step S22.

Step S23 is ended by this, and the processing proceeds to Step S24.

Step S24 is a step where the display on the monitor 28 is shifted to a screen of various measurement modes, and a measurement result is displayed on the monitor 28, using the information saved in Step S23.

In Step S24, the three-dimensional shape of the subject displayed on the bright field image is displayed on the monitor 28, by overlaying the result analyzed in Step S23 on the bright field image (or bright field image acquired in Step S19) acquired in Step S3. This enables the user to know the three-dimensional shape of the subject.

Step S24 is ended by this, and a series of processes is ended.

Step S26 is a step that branches from the above Step S22, and is a step that performs information processing required to display the measurement result later.

In Step S26, similar to the above Step S23, the three-dimensional shape is analyzed on the basis of the pattern projection images stored in the RAM 24. For example, in the second embodiment, the three-dimensional shape of the subject is analyzed by the well-known spatial phase shift method or Fourier transform method, using one sheet of a pattern projection image.

Additionally, analysis results of the bright field image, the pattern projection image, and the three-dimensional shape and optical parameters used for the analysis are saved as binary files or text files, respectively, in the auxiliary storage device 25. In this case, by making portions of file names common or collectively saving these files in one directory (folder), these files are saved in the auxiliary storage device 25 so that the files can be collectively read later.

Step S26 is ended by this, and a series of processing is ended.

As described above, according to the measuring method of the second embodiment of the present invention, the three-dimensional shape of a subject can be measured on the basis of one sheet of a pattern projection image captured in a state where a predetermined fringe pattern is projected onto the subject. Thus, the three-dimensional shape can be measured in a short time using the endoscope apparatus 1.

According to the measuring method of the second embodiment of the present invention, even in an environment where a fringe pattern is projected from one projection window 13 in the endoscope apparatus 1 in which the diameter of the insertion section 10 is reduced, a three-dimensional shape can be measured with high precision.

Since deviation can be detected by capturing a bright field image in addition to one sheet of a pattern projection image and using two sheets of images selected from the pattern projection image and the bright field image, the measurement precision of a three-dimensional-shape can be enhanced.

Since bright field images are respectively captured before and after one sheet of a pattern projection image is captured, and used for deviation detection, the absence and presence of deviation can be determined with high precision.

In the measuring method of the second embodiment of the present invention, deviation is detected using bright field images before and after a pattern projection image is captured, and a three-dimensional shape is analyzed when it is determined that there is no deviation. Thus, analysis is not performed with fringe patterns on a plurality of pattern projection images deviated. For this reason, the analysis precision of the three-dimensional shape can be enhanced. Moreover, the positional deviation when the measurement result using the pattern projection image is overlaid and displayed on the bright field images can also be reduced.

Modification of the Second Embodiment

Next, a modification of the measuring method according to the above-described second embodiment will be described.

In the present modification, the measuring method of the three-dimensional shape measurement of a subject is different. The measuring method of the present modification will be described below mainly about points that are different from the above-described second embodiment in terms of processing contents.

In the present modification example, the three-dimensional shape is analyzed in Step S23 and Step S26 by an optical cutting method, using one sheet of a pattern projection image. In the present modification, the three-dimensional shape is analyzed on one pattern, using one sheet of a pattern projection image. Therefore, as compared to the case where the entire surface of one sheet of a pattern projection image is analyzed in the above-described embodiment, a portion where the three-dimensional shape can be measured is limited, but analysis time can be significantly shortened.

Although the second embodiment of the present invention has been described above in detail with reference to the drawings, specific configuration is not limited to the embodiment, and design changes are also included without departing from the scope of the present invention.

For example, the above-described second embodiment has been described using the example in which one sheet of a pattern projection image is captured. However, substantially one sheet of a pattern projection image may be acquired and used for analysis by capturing a plurality of sheets of pattern projection images and selecting one sheet of a pattern projection image whose state is good.

Although the example in which the two sheets of bright field images are selected as the images to be used in order to detect any deviation is shown in the above-described second embodiment, pattern projection images may be used as the images to be used in order to detect any deviation. Additionally, bright field images more than two sheets of images may be captured. If there are bright field images more than two sheets of images, any deviation can be detected by selecting a required number of sheets of images from the bright field images if necessary.

The elements shown in the above-described second embodiment and respective modifications can be suitably combined.

What is claimed is:

1. An endoscope apparatus that measures a subject using a pattern projection image of the subject on which a light and dark pattern of light is projected, the endoscope apparatus comprising:
   an insertion tube having a central axis;
   an image sensor that is provided to acquire an image of the subject;
   an objective optical system that is provided to form the image of the subject on the image sensor;
   an illumination light source that emits illumination light to illuminate the subject;
   a pattern projector that projects the light and dark pattern onto the subject;
   a projection window that is disposed at a distal end portion of the insertion tube for the pattern projector, the distal end portion of the insertion tube being divided into two sides by a first imaginary plane that is defined to include the central axis of the insertion tube, and a center of the projection window being disposed at one of the two sides of the distal end portion of the insertion tube in a front view of the distal end portion of the insertion tube;
   an illumination window through which the illumination light is emitted from the illumination light source; and
   an observation window which is disposed at the distal end portion of the insertion tube for the objective optical system, a center of the observation window being disposed at an opposite side of the center of the projection window with respect to the first imaginary plane in the front view of the distal end portion of the insertion tube,
   wherein, with respect to a second imaginary plane that is defined to include both the center of the projection window and the central axis of the insertion tube and that is perpendicular to the first imaginary plane in the front view of the distal end portion of the insertion tube, (i) the illumination window is disposed to be spaced from the second imaginary plane so as to be farther from the central axis of the insertion tube in a radial direction than the observation window, and (ii) the observation window is disposed such that the center of the observation window is offset relative to the first imaginary plane and the second imaginary plane.

2. The endoscope apparatus according to claim 1, wherein a center of the illumination window is disposed at an opposite side of the center of the observation window with respect to the second imaginary plane.

3. The endoscope apparatus according to claim 2, wherein a number of the projection window is one.

4. An endoscope apparatus that measures a subject using a pattern projection image of the subject on which a light and dark pattern of light is projected, the endoscope apparatus comprising:

an insertion tube having a central axis;

an image sensor that is provided to acquire an image of the subject;

an illumination light source that emits illumination light to illuminate the subject;

a pattern projector that projects the light and dark pattern onto the subject;

a projection window that is disposed at a distal end portion of the insertion tube for the pattern projector, the distal end portion of the insertion tube being divided into two sides by a first imaginary first plane that is defined to include the central axis of the insertion tube, and a center of the projection window being disposed at one of the two sides of the distal end portion of the insertion tube when the projection window is viewed from a front view;

an illumination window through which the illumination light is emitted from the illumination light source; and an objective optical system that is provided at the distal end portion of the insertion tube to form the image of the subject on the image sensor, an optical axis of the objective optical system being disposed at an opposite side of the center of the projection window with respect to the first imaginary plane when the projection window is viewed from the front view, wherein, with respect to a second imaginary plane that is defined to include both the center of the projection window and the central axis of the insertion tube and that is perpendicular to the first imaginary plane when the projection window is viewed from a front view, (i) the illumination window is disposed to be spaced from the second imaginary plane so as to be farther from the central axis of the insertion tube in a radial direction than the objective optical system, and (ii) the objective optical system is disposed such that the optical axis of the objective optical system is offset relative to the first imaginary plane and the second imaginary plane.

5. The endoscope apparatus according to claim 4, wherein a center of the illumination window is disposed at an opposite side of the optical axis of the observation optical system with respect to the second imaginary plane.

6. The endoscope apparatus according to claim 5, wherein a number of the projection window is one.

* * * * *